United States Patent
Vija et al.

(10) Patent No.: US 12,394,119 B2
(45) Date of Patent: *Aug. 19, 2025

(54) DATA DRIVEN RECONSTRUCTION IN EMISSION TOMOGRAPHY

(71) Applicant: Siemens Medical Solutions USA, Inc., Malvern, PA (US)

(72) Inventors: Alexander Hans Vija, Evanston, IL (US); Francesc dassis Massanes Basi, Chicago, IL (US); Manjit Ray, Hoffman Estates, IL (US); Raymond Shi Xu, Inverness, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/937,468

(22) Filed: Oct. 3, 2022

(65) Prior Publication Data
US 2023/0036485 A1  Feb. 2, 2023

Related U.S. Application Data

(62) Division of application No. 16/946,212, filed on Jun. 10, 2020, now Pat. No. 11,494,955.

(51) Int. Cl.
*G06T 11/00* (2006.01)
*G06T 7/11* (2017.01)
*G06T 11/20* (2006.01)

(52) U.S. Cl.
CPC .............. *G06T 11/008* (2013.01); *G06T 7/11* (2017.01); *G06T 11/006* (2013.01);
(Continued)

(58) Field of Classification Search
CPC ..... A61B 6/037; A61B 6/5205; A61B 6/5264; G06T 7/11; G06T 11/006; G06T 11/008;
(Continued)

(56) References Cited

U.S. PATENT DOCUMENTS 5,489,782 A  2/1996  Wernikoff
5,552,606 A  9/1996  Jones et al.
(Continued)

OTHER PUBLICATIONS

Defrise et al. "Image reconstruction algorithms in PET." Positron emission tomography: basic sciences. London: Springer London, 2005. 63-91. (Year: 2005).*

(Continued)

*Primary Examiner* — Katrina R Fujita

(57) ABSTRACT

For controlling reconstruction in emission tomography, the quality of data for detected emissions and/or the application controls the settings used in reconstruction. For example, a count density of the detected emissions is used to control the number of iterations in reconstruction to more likely avoid over and under fitting. The count density may be adaptively determined by re-binning through pixel size adjustment to find a smallest pixel size providing a sufficient count density. As another example, the detected data may have poor quality due to motion or high body mass index (BMI) of the patient, so the reconstruction is set to perform differently (e.g., less smoothing for high motion or a different number of iterations for high BMI). The quality of the data may be used in conjunction with the application or task for imaging the patient to control the reconstruction.

16 Claims, 3 Drawing Sheets

(52) U.S. Cl.
CPC .. *G06T 11/203* (2013.01); *G06T 2207/10104* (2013.01); *G06T 2207/10108* (2013.01); *G06T 2211/424* (2013.01)

(58) Field of Classification Search
CPC ......... G06T 11/203; G06T 2207/10104; G06T 2207/10108; G06T 2211/412; G06T 2211/424
See application file for complete search history.

(56) References Cited

U.S. PATENT DOCUMENTS

| | | | | |
|---|---|---|---|---|
| 8,787,521 | B2* | 7/2014 | Thibault | G06T 11/006 378/20 |
| 10,058,287 | B2* | 8/2018 | Meyer | G01R 33/5611 |
| 10,679,356 | B2 | 6/2020 | Muraoka et al. | |
| 2008/0226149 | A1 | 9/2008 | Wischmann et al. | |
| 2009/0037130 | A1* | 2/2009 | Feiweier | A61B 90/36 702/104 |
| 2009/0148019 | A1 | 6/2009 | Hamada et al. | |
| 2009/0154641 | A1* | 6/2009 | Thielemans | G01T 1/1647 382/131 |
| 2010/0067765 | A1* | 3/2010 | Buther | G16H 50/30 382/131 |
| 2010/0155608 | A1 | 6/2010 | Devito et al. | |
| 2010/0166274 | A1* | 7/2010 | Busch | G06T 11/006 382/131 |
| 2010/0220909 | A1* | 9/2010 | Thielemans | G06T 11/005 382/131 |
| 2012/0018645 | A1 | 1/2012 | Vija | |
| 2012/0089015 | A1* | 4/2012 | Gagnon | A61B 6/037 600/425 |
| 2012/0201428 | A1* | 8/2012 | Joshi | G06T 11/006 382/107 |
| 2014/0276029 | A1* | 9/2014 | Wollenweber | A61B 6/5264 600/428 |
| 2015/0063670 | A1 | 3/2015 | Hamada et al. | |
| 2015/0119703 | A1* | 4/2015 | Mitchell | A61B 6/5294 600/425 |
| 2015/0289826 | A1* | 10/2015 | Herold | A61B 6/0407 378/209 |
| 2017/0091963 | A1* | 3/2017 | Panin | A61B 6/5264 |
| 2018/0315225 | A1* | 11/2018 | Zhang | G06T 7/0012 |
| 2019/0133542 | A1* | 5/2019 | Li | A61B 6/5247 |
| 2019/0290228 | A1 | 9/2019 | Vija | |
| 2019/0378312 | A1* | 12/2019 | Wang | G06T 11/005 |
| 2020/0008770 | A1* | 1/2020 | Salomon | G06T 7/20 |
| 2020/0093454 | A1 | 3/2020 | Vija et al. | |
| 2020/0170588 | A1 | 6/2020 | Tai et al. | |
| 2020/0175732 | A1 | 6/2020 | Andreyev et al. | |
| 2022/0022834 | A1 | 1/2022 | Nehmeh et al. | |

OTHER PUBLICATIONS

Alessio et al. "Application and evaluation of a measured spatially variant system model for PET image reconstruction." IEEE transactions on medical imaging 29.3 (2010): 938-949. (Year: 2010).

Andersson, Jesper LR. "How to obtain high-accuracy image registration: application to movement correction of dynamic positron emission tomography data." European journal of nuclear medicine 25.6 (1998): 575-586. (Year: 1998).

Cheng et al. "Quantitative accuracy of MAP reconstruction for dynamic PET imaging in small animals." Medical physics 39.2 (2012): 1029-1041. (Year: 2012).

Lamare et al. "List-mode-based reconstruction for respiratory motion correction in PET using non-rigid body transformations." Physics in Medicine & Biology 52.17 (2007): 5187. (Year: 2007).

Ivanovic et al. "Evaluation of PET standard uptake values dependence on imaging protocols for dual time point imaging." IEEE Symposium Conference Record Nuclear Science 2004.. vol. 7. IEEE, 2004. (Year: 2004).

Qian et al. "Image reconstruction in rectangular PET systems using distance-driven projections." 2013 IEEE Nuclear Science Symposium and Medical Imaging Conference (2013 NSS/MIC). IEEE, 2013. (Year: 2013).

Vija, A. Hans, Siemens Healthineers, and Molecular Imaging Business Line. "xSPECT reconstruction method." White Paper Order A91MI-10462 (2017): T1-7600. (Year: 2017).

Zeintl et al. "Quantitative accuracy of clinical Tc-99m SPECT/CT using OSEM-3D with attenuation and scatter correction." (2010): 583-583. (Year: 2010).

* cited by examiner

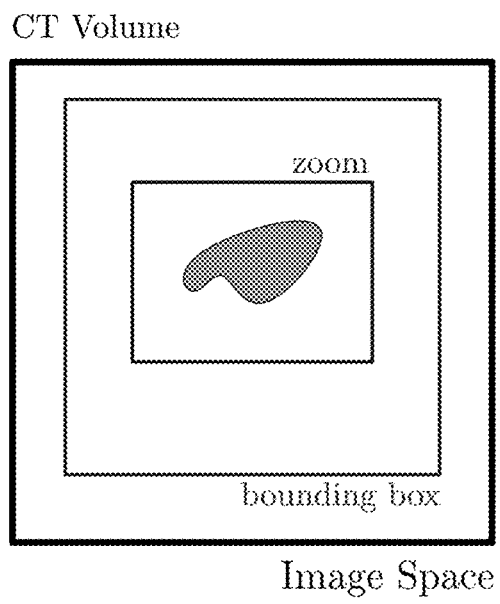
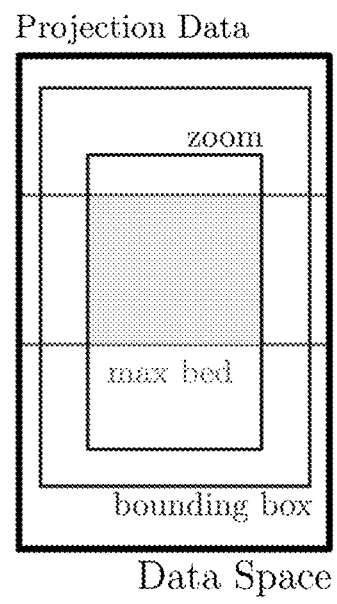
FIG. 2A
FIG. 2B
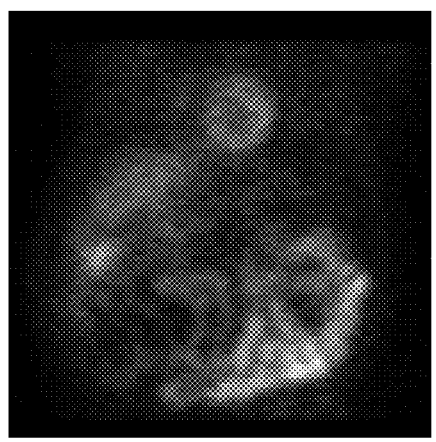
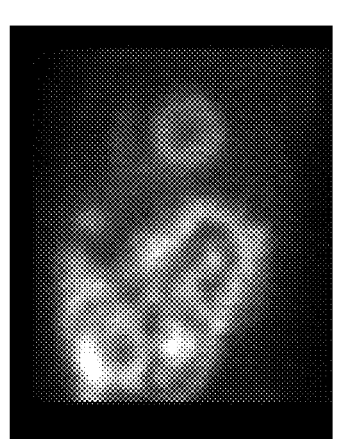
FIG. 3A
FIG. 3B

DATA DRIVEN RECONSTRUCTION IN EMISSION TOMOGRAPHY

RELATED APPLICATION

This application is a divisional of U.S. application Ser. No. 16/946,212, filed Jun. 10, 2020, which is hereby incorporated by reference in its entirety.

BACKGROUND

The present embodiments relate to emission tomography or other nuclear medical imaging. Example tomography imaging modalities include single photon emission computed tomography (SPECT) and positron emission tomography (PET). A radioactive substance is administered to a patient. An imaging scanner detects the y-radiation emitted from the patient.

The detected emissions are tomographically reconstructed to generate an image object of locations of the emissions in a patient. An image of the patient for diagnosis or to confirm therapy dose is generated by tomographic reconstruction. Using forward projection of detected emissions and back projections of residuals, a representation of the emissions from the patient is iteratively created. Too many iterations may lead to over-fitting, enhancing noise in the image. Too few iterations may lead to less resolution or poor fitting. In many cases, the number of iterations is either suggested through tables that consider the number of total counts and the clinical purpose of the scan or it is manually designated by the user. The number of iterations or other reconstruction parameters may not be optimized for imaging a given patient.

SUMMARY

By way of introduction, the preferred embodiments described below include methods, systems, and non-transitory computer readable media for controlling reconstruction in emission tomography. The quality of data for detected emissions and/or the application controls the settings used in reconstruction. For example, a count density of the detected emissions is used to control the number of iterations in reconstruction to more likely avoid over and under fitting. The count density may be adaptively determined by re-binning through pixel size adjustment to find a smallest pixel size providing a sufficient count density. As another example, the detected data may have poor quality due to motion or high body mass index (BMI) of the patient, so the reconstruction is set to perform differently (e.g., less smoothing for high motion or a different number of iterations for high BMI). The quality of the data may be used in conjunction with the application or task for imaging the patient to control the reconstruction.

In a first aspect, a method is provided for controlling reconstruction in an emission tomography system. The emission tomography system acquires counts of emissions from a patient. A pixel size for framing the counts is set based on a count density. An object representing the emissions within the patient is reconstructed from the counts as framed using the set pixel size. The number of iterations of the reconstruction is based on the count density. The number of iterations may be based on the application as well. An image is generated from the reconstructed object.

In a second aspect, a method is provided for controlling reconstruction in an emission tomography system. The emission tomography system acquires counts of emissions from a patient. The counts are adaptively framed by re-binning the counts. The adaptive framing increases a size of a data matrix based on a first measure, such as BMI, count density, or motion. A representation of function in the patient is reconstructed from the counts as re-binned in the adaptive framing. An image of the representation of function is generated.

In a third aspect, a nuclear imaging system includes a detector configured to detect emissions from a patient. An image processor is configured to receive an application for imaging, determine a reconstruction-related quality characteristic of the detected emissions, to set a value of a reconstruction parameter based on the reconstruction-related quality characteristics and the application, and to reconstruct a representation from the emissions using the value of the reconstruction parameter. A display is configured to display an image of the representation.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIGS. 2A and 2B illustrate adaptive framing using a region of interest relative to anatomy and/or emission tomography system bed position;

FIGS. 3A and 3B are example SPECT images with different count densities; and

DETAILED DESCRIPTION OF THE DRAWINGS AND PRESENTLY PREFERRED EMBODIMENTS

Figure 1:
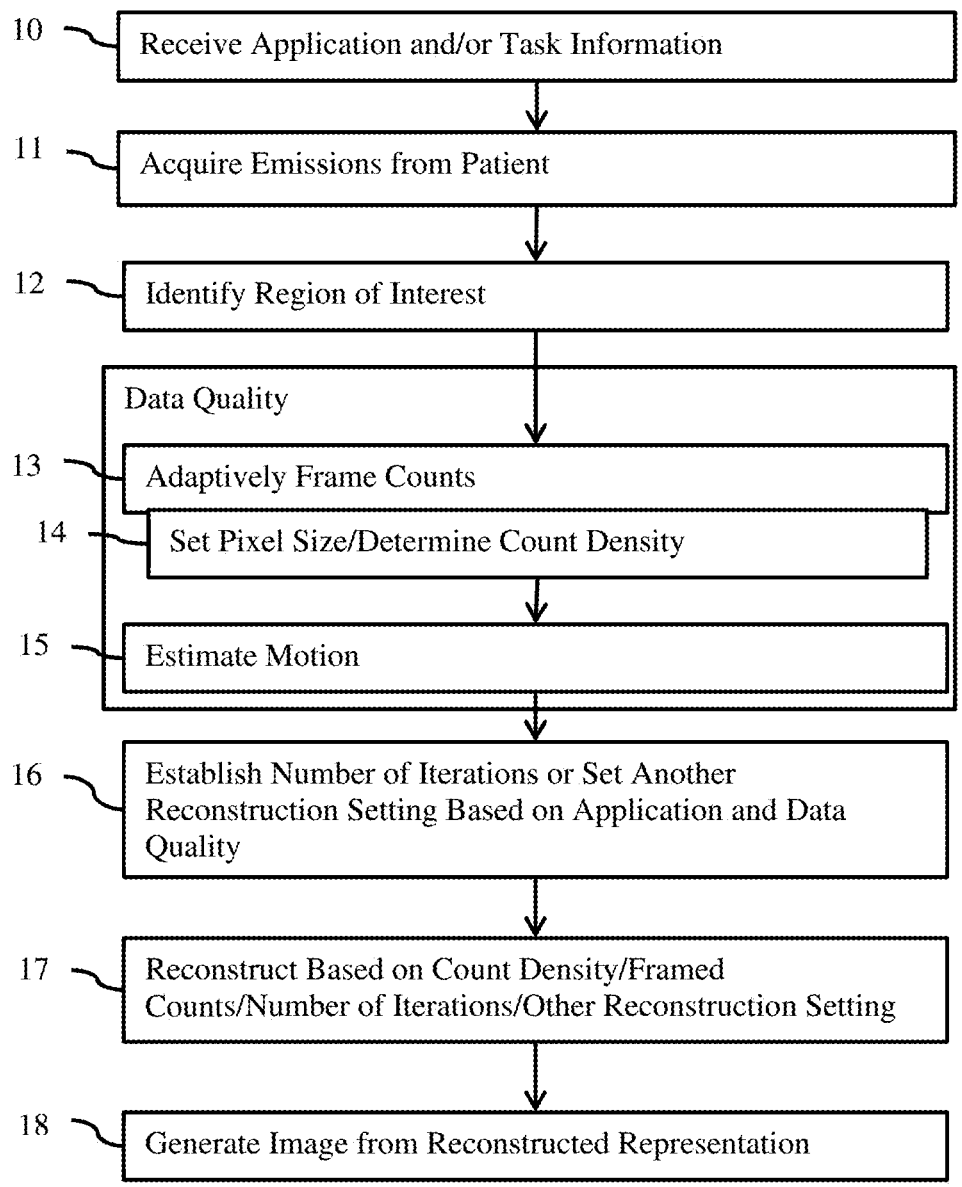
FIG. 1 is a flow chart diagram of one embodiment of a method for controlling reconstruction in an emission tomography system.

Data-space driven parameters are used in application-specific reconstructions. An automatic algorithm, data and application driven, determines the number of iterations or other reconstruction setting to achieve good image quality. The quality of the acquired data and the clinical purpose of the scan are analyzed to decide how many iterations of the reconstruction would provide good, task-based, image quality. Over-iteration or under-iteration, which effect the task-based image quality of the reconstructed data, may be avoided or limited. The quality of the acquired data and the clinical purpose of the scan are analyzed to decide one or more settings for reconstruction, such as the iterative processor to use (e.g., conjugate gradient or expectation minimization with or without gating) or the image formation or compensation settings (e.g., system model, motion correction, attenuation correction, and/or scatter correction).

The application provides an indication of a quality level and/or information used in measuring quality of the detected emissions. Different applications have different end goals of the reconstruction, so the needs of the data quality may vary by application. The data quality of the detected emissions may be used with the strengths and weaknesses of different reconstruction to configure the reconstruction. The user may have minimal input or control, such as indicating a type of iterative processor (e.g., update process) and/or another setting (e.g., full width half maximum setting). By using data quality and application, a reconstructed object may more likely provide a useful image. Reconstruction optimization based on the reconstructed object may also be used.

In one embodiment, the number of iterations needed for a reconstruction is determined by analyzing the number of counts in data space. The data is framed to have a number of counts per pixel (count density) that enable good image quality on the reconstruction, and then the number of iterations is determined from the count density. The number of iterative updates required to achieve good image quality is data dependent, as a minimum number of counts per pixel (density) is needed to achieve good image quality. Use of the adaptive pixel size setting (i.e., adaptive framing) and/or count density to control reconstruction may avoid reconstruction errors provided where the user controls the number of iterations or other reconstruction setting.

The measurement indicating data quality, such as count density, motion, or BMI, may be used to directly set the value of the reconstruction parameters, such as the number of iterations (e.g., updates) and/or amount of smoothing (temporal and/or spatial) to be used. For example, the count density is determined, and a look-up table provides the number of updates (iterations) based on the count density. In another approach, an adaptive process is used to set the reconstruction based on data quality. For example, different possible pixel sizes are tested, where the largest pixel size resulting in a sufficient count density is used for framing. The application or task may determine limits or goals for the pixel size through the desired voxel size.

FIG. 1 shows one embodiment of a flow chart of a method for controlling reconstruction in an emission tomography system. The data quality and/or application is used to control the reconstruction, such as using count density or adaptive framing to control the number of iterations. The application and/or task for the imaging may be used in the control of reconstruction, providing automated setting of values of reconstruction parameters in a way less reliant on more error prone user control.

Figure 4:
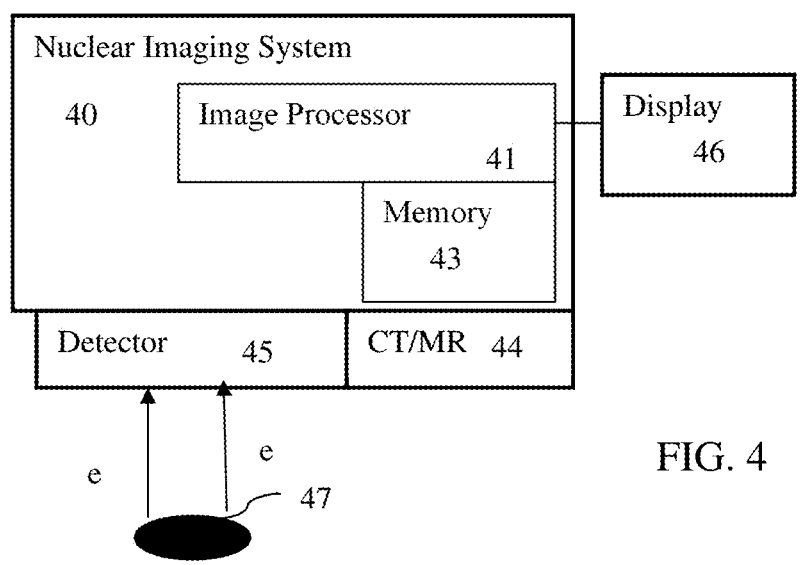
FIG. 4 is a block diagram of a nuclear imaging or emission tomography system, according to one embodiment.

The method is implemented by a emission tomography or nuclear imaging system, such as a PET or SPECT system. In one embodiment, the system of FIG. 4 is used. A user interface is used for act 10, where the image processor receives the input. A detector performs act 11. The user interface and/or image processor perform act 12. Acts 13-18 are performed by the image processor. A display device may be used for act 18. Other devices may perform and/or be used for the various acts.

The acts are performed in the order shown (i.e., numerical or top to bottom) or other orders. For example, act 10 may be performed after acts 11 and/or 12. As another example, act 16 may be performed as part of act 13. In yet another example, act 15 may be performed before act 13.

Additional, different, or fewer acts may be provided. For example, acts 10 and/or 12 are not provided. As another example, only one or two of acts 13-16 are provided. In yet another example, act 18 is not provided, such as where the reconstructed object is used for imaging or therapy control rather than imaging. In other examples, acts for positioning the patient, configuring the scan by the emission tomography system, adding the radiopharmaceutical to the patient, diagnosis, and/or therapy are provided.

In act 10, the image process receives an indication of an application and/or task for the acquisition of detected emissions. The indication is received through the user interface, such as a user input device. The indication may be received from memory, such as from a patent medical record and/or imaging scheduler, or from a communications network interface.

The input is information from a treating or ordering physician or a radiologist. The input is a type of emission tomography scan and/or other goal (i.e., task) for the emission tomography scan. The type of emission tomography scan is an application, such as anatomy or disease-based application. For example, cardiology, neurology, oncology, whole-body, head, or general types are possible. More specific types may be input, such as a myocardial perfusion type of the cardiology type of emission tomography scan. Other identifications of the application may be used, such as identifying the anatomy of interest. Different applications may use different reconstruction settings and/or desired output specifications (e.g., voxel size and/or image matrix size).

A task (goal) or information may be input instead of or in addition to the application. A goal, such as the total amount of time to scan (e.g., 5 minutes for a claustrophobic patient) may be used. Another goal may be the desired resolution, contrast, or resolution and contrast tradeoff. The task may be a purpose for the imaging, such as lesion or infection detection. Different tasks, application, and/or other information may result in different reconstruction settings. The task and/or application may provide a desired image data matrix and corresponding voxel size, which may be used in determining reconstruction settings.

Patient information may be received. For example, the age, weight, height, sex, BMI, and/or other characteristic of the patient is received. A dose, type of isotope available, or other physician-related input may be provided.

The tasks, goals, and/or other information may determine desired characteristics of imaging. For example, the resolution, contrast, or another characteristic may be different for different tasks and/or applications. The task and/or application may set a desired image matrix (i.e., size of area or volume) and corresponding image unit size (e.g., pixel or voxel size for the image matrix). Alternatively, the user inputs the desired image matrix and/or image unit size.

The framing of the data for the detected emissions establishes a data matrix and pixel size in the projection domain. The data matrix and pixel size relate to the image matrix and image unit size. To provide the desired characteristics of the reconstructed object as defined by the image matrix and the image unit size, the detected data is framed to provide sufficient data matrix and pixel sizes. Different data matrices and pixel sizes may provide the desired image matrix and image unit size.

In act 11, the emission tomography system detects emissions from the patient. After ingesting or injecting a radiotracer into the patient, the patient is positioned relative to a detector, and/or the detector is positioned relative to the patient. Once the patient has been prepared and readied, the scan commences, and thus data is acquired.

The emission tomography system scans the patient based on settings. For example, the start position, dwell time, step size, collimator position, and/or other aspects of a SPECT scan control the operation of the system.

Emissions from the radiotracer within the patient are detected over time. A collimator in front of the detector limits the direction of photons detected by the detector, so each detected emission is associated with an energy and line of response (e.g., a cone of possible locations from which the emission occurred). For SPECT, the detector may be rotated or moved relative to the patient, allowing detection of emissions from different angles and/or locations in the patient, or any other way of creating a tomographically suited dataset from single photon emissions. In PET, the detector is formed in a ring so that coincidence is used to detect the same emission from different directions along the lines of response.

The emission detector includes direct detection with CZT or indirect conversion (e.g., NaL, LSO layered scintillation crystal) using photomultiplier tubes, SiPM, or other photon detectors. For SPECT, the photon detectors are arranged along a rectangular or other grid to provide a two-dimensional planar array for detecting gamma radiation. For PET, the detectors are arranged in a ring around a patient. Other types of detectors and detector arrangements may be used, such as any gamma detector.

The detected emissions over time are counted. The number of emissions for each line of response (LOR) and/or position on the detector are counted. The count may be for the entire detector rather than LOR. This acquired data of detected emissions is binned by LOR and/or location on the detector as an initial framing or a framing based on the detector.

In act 12, the image processor and/or user identify a region of interest. Rather than using all of the detected data, only detected data for a region of interest is used. For example, only detected data for LORs through particular anatomy is used. A computed tomography or other anatomy scanner images anatomy of the patient. Segmentation is applied to identify an anatomy of interest. After registration of the detected emissions to the anatomy, the LORs for the anatomy of interest are identified. As another example, only emissions detected at a given bed position are used, such as selecting counts for a bed position in which the most counts were detected. In other examples, the LORs with the greatest number of counts from any bed or camera position are used.

In one embodiment, the region is identified as an intersection of the anatomy of interest with a bed position of the emission tomography system having a maximum number of the counts. FIGS. 2A and 2B show an example. In FIG. 2A, a bounding box, segmentation, or zoom area relative to the anatomy of interest is defined, such as a box in or segmentation from a CT or X-ray image. As shown in FIG. 2B, the area of data space (detected emissions) that contains counts relevant to the clinical task is identified, such as the bed position with the maximum number of counts. The intersection (see grayed area in FIG. 2B of zoom or bounding box with bed position) of the area of the data space with the designator of the anatomy of interest is the region of interest (ROI). The intersection combines the image space designation (e.g., anatomy) with data space designation (e.g., LORs or counts by bed position). The detected data for LORs or count in this ROI and not LORs or counts from outside the ROI is used to detect data quality.

In other embodiments, the image space mask is based on a Mu-map where CT imaging is available. Where CT imaging is not available, a union of orbit mask per bed is used as the image space mask. The image mask is forward projected per view per bed and thresholded to identify the ROI or LORs in the ROI. Other ROI designations to identify the counts (detected data) to use may be used. In another alternative, all of the detected data is used.

In another embodiment, only emissions detected at certain locations on the gamma camera or detectors are used. The application or task may indicate a sub-set of locations on the detector to use, such as only locations with a count above a threshold level or only location associated with LORs for particular anatomy. In a brain application, the counts for some detector locations may be low due having LORs not intersecting the brain. The detected data only for the ROI (e.g., brain) is identified and selected to avoid alteration of the reconstruction settings based on a lack of emissions from locations not of interest.

The ROI may be used in determining the quality of the acquired data. Rather than or in addition to testing quality of a reconstructed object, the quality of the emission data (e.g., counts) is determined. Due to changes in settings by users (e.g., turning off attenuation and scattering or motion compensation), motion of the patient, poor fitting system model, environmental effects, the tissue being imaged, or another variance, the data quality may be less. Based on the application and the quality of data, the reconstruction (e.g., iterative process used and/or image formation settings) may be automatically altered to provide the best or better reconstructed object for that application given the quality of the data. Acts 13 and 14 are directed to an example where quality is based on count density for the ROI. Act 15 is directed to an example where quality is based on an amount of motion captured in the data (e.g., limit number of updates or iterations to avoid adding additional smearing due to motion artifacts in the captured counts).

In act 13, the image processor adaptively frames the counts by re-binning the counts. Using the ROI-based detected data, the counts may be re-binned, providing a different data matrix and/or pixel size in the data domain. In alternative embodiments, adaptive re-binning is not used, such as where count density directly maps to the reconstruction parameter for reconstruction from the detected data as initially framed.

The data matrix is based on the pixel size. The pixel size for the detected counts may be changed. As a result, more or fewer counts are assigned to each pixel or LOR. A larger pixel size results in a smaller data matrix. Some example data matrix sizes are 128, 256, . . . up to a data matrix using the smallest pixel size. The adaptive framing re-bins the counts, increasing a size of the data matrix and providing a smaller pixel size.

The adaptive framing is based on a measure of the quality of the data. The quality of the detected emissions is measured directly, such as by count density or motion (e.g., change in number of LORs with counts over a threshold over time). The quality of the detected emissions may be measured indirectly, such as by a characteristic of the patent (e.g., BMI, age, or sex). The measure is used to select a data matrix size (e.g., look-up table of measure to pixel size) or used as a check as different data matrix sizes are tested.

In one embodiment at act 14, the pixel size is set for framing the counts based on a count density. Using the counts for the region of interest, and not counts for other regions, the count density is determined. For example, only the counts along the LORs for the intersection of the imaged anatomy of interest and data space for the bed position with the maximum number of counts are used.

The image space resolution is to be provided as appropriate for the task and/or application or maximized while keeping the count density large enough to achieve good image quality. The image space resolution is based, at least in part, on the data space pixel size. Smaller pixel sizes provide greater resolution than larger pixel sizes. The good image quality is based on expert input and/or clinical studies. The quality information is used to map the count density to quality, so that different count densities are desired in different applications to provide sufficient quality. Then, depending on what count density is provided by the detected data and the task-based reason for the reconstruction, the number of updates or other reconstruction setting for the reconstruction is selected or set. The setting may be specific to the reconstruction algorithm used (e.g., conjugate gradient (CG) or expectation minimization (EM), attenuation and scatter correction (AS) or no AS, gated or non-gated, . . . ).

The count density is a number of counts per data space pixel. From the data in the ROI, how many pixels would this area turn out to be if the count density was preset is given by:

$$\# \text{ pixels} = \frac{\# \text{ counts}}{\rho}$$

where $\rho$ is the count density (1/sqmm). The number of pixels is from the data matrix where the pixel size determines the number of pixels in the re-binning.

Other count density functions may be used. For example, the count density may be determined based, at least in part, as the number of counts per pixel based on the type of tomography. For single bed tomography, the ROI is defined in each view (e.g., SPECT camera position). The total number of ROI pixels is counted. The total number of detected emissions (e.g., single or multiple photopeaks) within the ROI are counted in each view. The count density per pixel is the sum across views of the numbers of detected emissions divided by the sum across views of the total number of ROI pixels. For a multiple-bed type of tomography, the count density is determined from the bed position that has the most counts and/or a bed position covering more of the region of interest than any other bed positions. For a dynamic single bed type of tomography, the sums of the single bed tomography include summing across the rotations per volume. For a gated-single bed type of tomography, the sums are across all the gates. The resulting count density may be divided by the number of gates.

In one embodiment of adapting based on count density, different pixel sizes are tested to identify a smallest pixel size with a count density greater than a threshold. The threshold may be a default or may be based on the application or task. The counts are re-binned according to the smallest pixel size where the count density is above the threshold. The different possibilities for number of pixels and corresponding pixel size are scanned or searched. The smallest pixel size that has enough counts per pixel (density) to achieve a good image quality reconstruction is selected. The framing of the detected data used in reconstruction is set based on the count density.

The count density may alternatively or additionally be used to set the number of iterations used in reconstruction. After any adaptive framing or using a default or user-set framing, the count density of the data matrix to be used in reconstruction determines the number of iterations used in the reconstruction. Different count densities may be mapped to different numbers of iterations depending on the reconstruction algorithm being used. For example, a CGAS algorithm is used. The number of iterations is set to X for a low density above a threshold density, to X+N for a mid-range of densities, and to X+M for a higher range of densities where N and M are integers and M is greater than N. Any linear or non-linear mapping of density to number of updates may be used. Other ranges, number of ranges (e.g., two, three, or more than four), and/or numbers of iterations may be used. The number of iterations may be based on a clinical study or expert feedback for image quality given reconstruction with different numbers of iterations for each of the different count densities.

Different tables or mappings may be provided for different types of reconstruction. Alternatively, the same number of iterations are used regardless of the type of reconstruction. In one embodiment, one type of reconstruction is used as a base line to determine the number of iterations from the count density. Other types of reconstruction are assigned weights to determine the number of updates for that type of reconstruction based on the number determined from the standard type of reconstruction. For example, CGAS non-gated is the standard type. The number of iterations is selected as the standard number based on the count density and application. Where another type of reconstruction (e.g., CGAS gated, EMAS, or EMAS gated) is to be used, a look-up table or function converts the number of iterations for CGAS non-gated to the other type of reconstruction. The conversion may be by look-up table or a weight. For example, the number of updates is divided by or multiplied by a weight. In one embodiment, EMAS has a greater number of updates than CGAS non-gated for a same application, and CGAS gated has a fewer number of updates than CGAS non-gated for a same application.

The assignment of number of iterations may be application or task specific. Different weights relative to a standard may be used. Alternatively, different tables for the number of iterations based on density are used for different applications or tasks. In one embodiment, the application or task is used as a check or to override the number of iterations. Some applications may use a fixed number of updates, such as skeletal or wholebody for theranostics. Other applications, such as whole body diagnostics, brain, cardiac, or general may not be overridden or may have an acceptable range where a default low or high number of updates are used if exceeding the acceptable limits.

In one embodiment, the density of counts for projection is analyzed, and the data space is resized to maximize reconstruction resolution while keeping enough counts per pixel to guarantee good image quality. The intersection of the ROI with the detected data is used to bin the detected counts at a 128×128 data matrix. The detected data is then re-binned while increasing matrix size as long as the density of counts per pixel is higher than 1 or until the matrix is 1024×1024 or another threshold matrix size. If the density is then higher than 10 counts per pixel, 48 updates are used for reconstruction, otherwise 36 updates, and if the number of counts per pixel is smaller than 1, only 24 updates are used.

In another embodiment, a smallest one of the different sizes is selected as the pixel size as long as the respective count density for the pixel size is above a threshold level. The image (e.g., volume) matrix and image unit (e.g., voxel) size are received from the user or application selection. The user selects the image matrix size, and, if CT is absent, the zoom factor. If CT is present, anatomy segmentation and/or a bounding box are used. A volume voxel size for the object is calculated from the matrix size. If CT is present, the volume voxel size is the CT field of view (FOV) divided by the image matrix size. If CT is absent, the volume voxel size is: (nuclear medicine (NM) FOV/zoom)/image matrix size.

The data matrix and pixel size are then determined adaptively. An initial data matrix size is calculated from the volume voxel size, and an initial pixel size is calculated from the data matrix size. The data matrix size is initially set to 2^round (log 2(NM FOV/volume voxel size)), and the data pixel size is initially set to NM FOV/data matrix size. An initial count density per pixel is calculated from the initial data matrix size. The count density per pixel and ROI's is calculated at a fixed matrix size (e.g., 128). A count density per pixel at the initial data matrix size is calculated by rescaling the count density. A greatest data matrix size such that the count density is greater than threshold is found when the initial count density is below a threshold or the initial data matrix size is above a threshold. If the count density per pixel >1 or data matrix size <=128, the pixel size and data matrix size are selected for use. If the count density per pixel is <1 and the data matrix size is >128, then the highest data size in [128, 256, . . . , data matrix size] such that count density per pixel >1 is found. The initially computed count density is rescaled. The pixel size where the count density is above 1 (e.g., 1.0/square millimeter) is found. Other thresholds for count density and/or pixel size may be used, such as 0.1 for the count density. In one embodiment, 0.05/square millimeter, such as in four levels or ranges of (0.05, 0.1] (0.1, 0.5] (0.5, 1] (1, ∞] are used. 0.1/square millimeter may correspond, for example, to 5 mm×5 mm pixel to about 2-3 counts per pixel. Lower or ½ of that number of counts may be a cutoff for rebinning.

In addition to the number of iterations, the number of subsets may be determined based on the count density. The data may be sub-divided into different sub-sets, which are separately reconstructed where the results are then summed or averaged. The number of subsets may be used with the count density to determine the number of iterations. For example, the number of subsets is considered in determining the number of iterations based on the count density for CG and CGAS. The count density is divided into three ranges, such as [0,1.2] as level 1, [1.3,4) as level 2, and [4, ∞) as level three. The number of subsets and the count density level are used to look-up a number of updates, such as providing more updates for fewer subsets.

In other embodiments of setting the reconstruction based on data quality, the measurement of data quality is an amount of motion in act 15. The amount of motion is estimated from the counts, such as finding a magnitude of change in number of LORs with counts above a threshold over time or in a window. In one embodiment, projection images from different directions are obtained. A center-of-light location is found for each projection image. The fluctuation at the center-of-light locations is used as the measure of motion or used to derive a measurement of quality. U.S. Published Patent Application No. 2020/0093454 shows examples.

In act 15, various reconstruction parameters may be set based on the measured amount of motion given the application. The detected data may be re-binned (i.e., framed differently) based on the amount of motion. The number of iterations may be based on the detected motion, such as using fewer iterations for greater motion. The number of iterations may be based on just the amount of motion or based on both the amount of motion and the count density. The estimate of motion from the data may be used to determine the parameters needed for motion correction. The amount of motion may be used to determine volume and/or scatter projection estimate (SPE) smoothing level, such as the full width half maximum (FWHM) in mm. The setting of the reconstruction parameter from the motion estimate are used to achieve good or sufficient image quality in reconstruction.

The BMI or another characteristic of the patient (e.g., age, history, weight, . . . ) may be used as the measure. The patient characteristic may be used with or without count density to determine a number of iterations. Other reconstruction parameters may be set based on the patient characteristic. The setting of the reconstruction parameter from the patient characteristic are used to achieve good or sufficient image quality in reconstruction.

In act 16, one or more reconstruction settings are set (i.e., values to be used in reconstruction are determined) based on the application and/or data quality. The update process used, a variable of the update process (e.g., number of iterations), compensation (e.g., motion compensation, attenuation and scattering, and/or smoothing (FWHM)), or other image formation (e.g., variable of the system model) or another reconstruction characteristic is set automatically to account for the quality of data acquired by the scan or emission detection and to account for the application and corresponding end goal of imaging. The number of iterations in the update process (e.g., type of tomography or optimization) is used in the example of acts 16 and 17 below, but other variables may be set.

The image processor establishes the reconstruction parameter, at least in part, based on the application or task. For example, the number of iterations is based on the application and count density. As noted for Table III, the number of iterations may be set based on a check for override due to the application or task. The number of iterations from the look-up table addressed by count density for the selected pixel size (e.g., Table II) are used or overridden. In other embodiments, the application or task maps to a weight used to weight the determined number of iterations (either increasing or decreasing the number). In yet other embodiments, different tables of count density to number of iterations are provided for different applications or tasks. As another embodiment, the application or task determines a desired image matrix and corresponding image unit size, which is used to set the data matrix and pixel size for determining the count density.

In another embodiment, the re-binning or framing of act 13 is based on the task or application. Different thresholds for count density or matrix size may be based on the task or application.

Using the data quality to control reconstruction automates the selection of reconstruction parameters. The operation and control of the emission tomography system may be simplified for the user, and the risk of user error may be decreased. In the example of setting the number of iterations based on a measure of data quality, over- or under-iteration may be avoided. Over or under smoothing may be avoided. The image quality of the reconstruction may be improved or more consistent.

In act 17, the image processor reconstructs a representation of function in the patient from the counts as re-binned in the adaptive framing. The reconstruction is defined by the type of reconstruction, a relative contrast-to-resolution, and a stop criterion. Different types of reconstruction include CG, CGAS, EM, EMAS, filtered back-projection, iterative reconstruction, multi-modal reconstruction, Maximum Likelihood Expectation Maximization (ML-EM), Ordered Subset Expectation Maximization (OSEM), penalized weighted least squares (PWLS), Maximum A Posteriori (MAP), multi-modal reconstruction, and/or non-negative least squares (NNLS). These types of reconstruction may be gated or non-gated. Anatomical segmentation in a multi-modal reconstruction may be used in the reconstruction to improve assignment of locations of emission based on anatomy. The relative resolution and contrast may be based on separate parameters or a parameter balancing the tradeoff.

The reconstruction is iterative. The image reconstruction processor uses a system matrix or projection operators to describe the properties of the nuclear imaging system and uses an iteratively improved data model to calculate the image object based on the data set of detected emissions. The iterative reconstruction forward projects a current estimate of the object or image (e.g., object or image space) to projection or data space using a system matrix or forward projector operators representing the detection. Since the detected emissions are in a projection space or data domain (e.g., generally known location in two-dimensions but not three), the forward projection of the current volume is compared to the detected or measured emissions. A difference or residual between the forward projection and the detected emissions is backward projected. This backward projection provides a gradient or change for the image object. The direction and step size are determined for the change and applied to update the image object. The process is then repeated for another iteration or update of the reconstruction.

The number of iterations is a stop criterion in the reconstruction. The reconstruction ceases once the number of updates (i.e., the number of forward/backward projections have been performed) is reached or surpassed. The number of iterations set based on the count density and/or other measurements of data quality is used to control the forward/backward projection repetition. The current image object or representation of function or emissions from the patient is output. Once complete, an image object or representation, which may be an N-dimensional image object (typically N=3 in medical imaging applications), results.

The reconstruction uses other reconstruction settings. The type of reconstruction, the values of variables used in reconstruction, motion correction settings, and/or other information used to control reconstruction are defined by the values of the reconstruction parameters. The update process and/or image formation settings may be set based on data quality and the application. One or more settings may use default values.

The object or representation of the spatial distribution of emissions within the patient are reconstructed from the counts. The reconstruction is from the detect data as framed. The selected pixel size and corresponding data matrix size are used in the reconstruction. The number of iterations and/or another reconstruction parameter are used to reconstruct from this framed data. For example, the count density is used to set the number of iterations. As another example, the smoothing applied within or post reconstruction is based on an amount of motion estimated from the detected data or another source (e.g., motion sensor, camera, and/or anatomical scanning).

In act 18, the image processor generates an image from the reconstructed object or representation. The image is generated as a frame of display data formatted for a display screen or a display format. The image is generated for transmission over a computer network, storage in memory, printing by a printer, and/or display on a display screen.

To display an emission tomography image on a display screen, the reconstructed object is rendered to the display. Where the object is reconstructed as three-dimensional, then three-dimensional rendering is used to collapse the object to a two-dimensional image. Surface, volume, path tracing, ray casting, alpha blending, maximum intensity projection, or other volume rendering may be used. Planar or multi-planar reconstruction may be used. Alternatively, the object or representation is reconstructed as a two-dimensional object. A two-dimensional image is generated from the object.

The generated image is mapped to display values, such as RGB color values. The mapped values are buffered and used to display the emission tomography image on the screen of the display. The image may include anatomical information, such as overlaying the emission tomography image on a CT or MR image. Alternatively, the emission tomography image is displayed without the CT or MR image.

Due to the measure of quality of the emission data to control the reconstruction, the reconstruction more likely optimizes the image to satisfy the goal or goals of the physician. Through control of the number of iterations, the time to reconstruct may be reduced while providing desired image quality. Any excess quality in the emission data is used to reduce the number of iterations. Over and under-fitting may be avoided. Rather than relying on a user who may or may not provide the optimized image for a given scan, the data-based determination of the reconstruction settings provides the optimized image, maximizing the image content relative to the goal, application, and/or patient.

FIG. 3A shows an example planar image of an object reconstructed from a density cardiac scan with an average of 30 counts per square mm on ROI. The data matrix size was increased by 2 without reducing image quality. FIG. 3B shows an example planar image of an object reconstructed from a "high count" density cardiac scan with an average of 150 counts per pixel on ROI. The data matrix size was increased by 4 without reducing image quality. The examples of FIGS. 3A and 3B used the standard or baseline reconstruction (e.g., CGAS non-gated) where the number of iterations is given and based on the adaptation of the data matrix size (e.g., three levels mapping to three different numbers of iterations where greater density allows for a greater number of iterations.

FIG. 4 shows one embodiment of a nuclear imaging system 40. The system 40 is a PET, SPECT, multi-modal emission tomography imaging system or another nuclear imaging system for detecting emissions due to radioactive decay in a patient. The nuclear imaging system 40 may provide qualitative or quantitative imaging. The reconstruction for imaging is controlled by the data quality, such as adaptively setting the pixel size or data matrix size, number of iterations, and/or another reconstruction parameter based on data quality (e.g., count density, amount of motion, and/or patient BMI).

The system 40 implements the method of FIG. 1 or another method. The treating physician enters an application, task, or another indication of the diagnostic, prognostic, or therapeutic reasons for performing emission tomography for the patient. Patient information is entered. Various reconstruction and/or scan settings may be entered, or default values used. Reconstruction settings may be determined based on the physician request, patient information, and data quality. The detected emissions and other scan output may be checked for quality. As a result, an image optimized to the patient, the system 40, and the physician reasons for imaging is generated without requiring the operator to use a less optimized standard or default settings.

The multi-modal nuclear imaging system 40 includes an image processor 41, a memory 43, a display 46, a detector 45, and a CT/MR system 44. The image processor 41, memory 43, and/or display 46 are part of the imaging system 40 with the detector 45, part of the emission tomography part of the system 40, part of the CT/MR part of the system 40, or are separate (e.g., a computer or workstation). Additional, different, or fewer components may be provided. For example, the system 40 is a computer without the detector 45 and/or separate from the CT/MR system 44. As another example, user input, patient bed, x-ray scanner, or other nuclear imaging-related devices are provided. Other parts of the system 40 may include power supplies, communications systems, and user interface systems.

The CT/MR system 44 is included where the system 40 is a multi-modality nuclear imaging system. The CT/MR system 44 is an anatomical imaging modality. The CT/MR system is one of CT or MR but may be another anatomical medical imaging modality (e.g., ultrasound). Anatomical information is acquired by scanning with x-rays or magnetic resonance. The anatomical information may be used for emission tomography, such as using segmentation of anatomy or tissue type for reconstruction of emissions with a greater spatial resolution.

The image processor 41 a general processor, digital signal processor, graphics processing unit, application specific integrated circuit, field programmable gate array, digital circuit, analog circuit, combinations thereof, or other now known or later developed device for controlling the operation of the system 40 and/or reconstructing an object from emissions. In one embodiment, a single hardware processor as the image processor 41 implements measurement of data quality, setting of reconstruction parameters, and reconstruction. In other embodiments, different parts of this process are hosted by or implemented by different processors of the image processor 41, such as a control processor for measuring data quality and setting the reconstruction parameters and a separate reconstruction processor for reconstructing the representation from the emissions using the set reconstruction parameters. The image processor 41 may be a distributed network of interconnected processors. The image processor 41 is configured by software, firmware, and/or hardware to perform specific acts.

The detector 45 is a gamma camera connected with a gantry. The gamma camera is a planar photon detector. Any now known or later developed gamma camera may be used, such as any SPECT camera. The gantry rotates the gamma camera about the patient. More than one gamma camera may be used, such as a dual camera system. Alternatively, the detector 45 is a ring of crystals or scintillators with photomultiplier tubes or other optical detectors. Other structures of detectors may be used, such as other PET detectors. Other components may be provided, such as a collimator. The detector 45 and other parts of the emission tomography system 40 are configured to scan of the patient 47 by detecting emissions e from the patient 47.

The nuclear imaging system 40, using the detector 45, detects emissions e from the patient 47 for measuring uptake or physiological function. During scanning of a patient 47, the detector 45 detects emission events, e. The emissions occur from any location in a finite source (i.e., the patient 47). The radiotracer in the patient 47 migrates to, connects with, or otherwise concentrates at specific types of tissue or locations associated with specific biochemical reactions. Thus, a greater number of emissions occur from locations of that type of tissue or reaction. The emission events are detected at different positions or angles relative to the patient, forming lines of response for the events. With a ring of detectors of PET, the emissions are detected along the lines of response without movement of the detector 45. With a gamma camera of SPECT, the emissions are detected along the lines of response based on camera position. The patient bed and/or camera may move to define a field of view relative to the patient.

The image processor 41 is configured to receive input of physician or imaging task, imaging application, and/or patient information. Input of a image matrix size and/or voxel size may be received. The input information is by manual entry with an input device, configuration of the imaging system 40, and/or by information from a scheduler and/or patient medical record.

The image processor 41 is configured to determine a reconstruction-related quality characteristic of the detected emissions. For example, a count density is determined. The count density of the detected emissions may be determined for a fixed, initial, or default pixel size, data matrix size, and/or framing. Alternatively, the count density is determined as part of adaptively setting the pixel and data matrix sizes using image matrix, voxel size, and/or other quality of output image information. Other measures of quality characteristic of the detected emissions may be used, such as amount of motion and/or patient characteristic (e.g., BMI). The task or application may be used to select the quality characteristic measure to use.

The image processor 41 is configured to set a value or values of a reconstruction parameter or parameters. The value or values are based on the reconstruction-related quality characteristics, such as using count density, amount of motion, and/or patient characteristic to set the number of iterations. The value or values may be set, at least in part, based on the quality characteristic and a task or application. The value or values are based on the application. Using a look-up table or other mapping of application and data quality, the value or values of the reconstruction setting are determined. For example, the task is lesion detection in a brain application, so the number of iterations is based on that application, task, and the count density (e.g., count density determines a base number of iterations, the application is used for an override check of the base number of iterations, and the task sets the voxel size used to adaptively set the framing that results in the count density).

The reconstruction parameter or parameters include the number of iterations. Alternatively or additionally, the amount of smoothing, type of smoothing, location in the process of the smoothing (within reconstruction or post reconstruction), motion correction parameters, and/or framing (e.g., data matrix and/or pixel size) are the reconstruction parameter or parameters set based on data quality.

The image processor 41 is configured to reconstruct from the detected emissions. Emission tomography is performed. The anatomy data from the CT/MR system 44 may be used in the reconstruction of the detected emissions.

Any reconstruction may be used to estimate the activity concentration or distribution of the tracer in the patient (i.e., quantitative or qualitative emission imaging). The reconstruction processor 41 accesses the detected emission events from the memory 43, from the detector 45, or buffers to reconstruct. The anatomy data may likewise be accessed. The detected emissions and anatomy data are used to reconstruct the distribution of the radioisotope in two or three dimensions. Forward and backward projection are used iteratively. The iterations continue until a stop or termination point is reached, such as performing a certain number of iteration.

The reconstruction is controlled by the reconstruction settings (e.g., number of iterations). In the number of iteration example, the reconstruction forward projects and back projects residuals once for each iteration. A set number of iterations, such as based on the count density, is used. For the smoothing or motion correction examples, the reconstruction includes smoothing and/or motion correction. The values for filter kernel, type of smoothing, motion correction setting, and/or other parameters are used in the reconstruction.

The reconstruction processor 41 generates one or more images based on the reconstruction. Any given image represents the emissions from the patient. The image shows the spatial distribution, such as with a multi-planar reconstruction or a volume rendering. For quantitative imaging, the image represents accurate measures (e.g., in Bq/ml) of the activity concentration. Alternatively or additionally, the image shows a quantity or quantities (e.g., alphanumeric) representing the activity concentration or specific uptake values for one or more locations or regions.

The display 46 is a CRT, LCD, plasma screen, projector, printer, or other output device for showing an image. The display 46 displays an image of the reconstructed representation (e.g., an object representing function in a volume).

The detected emission events, counts, location, scan information (e.g., generic scan settings), inputs, framing, pixel size, count density, reconstruction settings, patient information, application, task, and/or other information are stored in the memory 43. The memory 43 may store data at different stages of processing. The data is stored in any format.

The memory 43 is a buffer, cache, RAM, removable media, hard drive, magnetic, optical, database, or other now known or later developed memory. The memory 43 is a single device or group of two or more devices. The memory 43 is part of the nuclear imaging system 40 or a remote workstation or database, such as a PACS memory.

The memory 43 is additionally or alternatively a non-transitory computer readable storage medium with processing instructions. The memory 43 stores data representing instructions executable by the programmed image processor 41. The instructions for implementing the processes, methods, and/or techniques discussed herein are provided on non-transitory computer-readable storage media or memories, such as a cache, buffer, RAM, removable media, hard drive, or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for controlling reconstruction in an emission tomography system, the method comprising:
   acquiring, by the emission tomography system, counts of emissions from a patient;
   adaptively framing the counts by re-binning the counts, the adaptive framing increasing a size of a data matrix based on a first measure;
   reconstructing a representation of function in the patient from the counts as re-binned in the adaptive framing; and
   generating an image of the representation of function.

2. The method of claim 1 wherein adaptively framing comprises testing different pixel sizes to identify a smallest pixel size with a count density of the counts per pixel as the first measure being greater than a threshold, the counts re-binned according to the smallest pixel size.

3. The method of claim 2 wherein testing comprises determining different densities with the different pixel sizes and selecting the smallest pixel size of the different pixel sizes as the pixel size where the respective different density for the pixel size is above a threshold level and is the count density.

4. The method of claim 2 wherein testing comprises determining the smallest pixel size where the count density is above 1.0/square millimeter.

5. The method of claim 2 wherein reconstructing comprises performing conjugate gated or expectation maximization reconstruction from the counts distributed according to the smallest pixel size.

6. The method of claim 2 further comprising identifying a region of interest, and wherein testing the different pixel sizes is performed using the counts for the region of interest and not counts for other regions.

7. The method of claim 1 wherein reconstructing comprises reconstructing with a number of iterations set based on a count density as the first measure.

8. The method of claim 7 wherein reconstructing comprises iteratively fitting the representation to the counts, with the iterative fitting ceasing after the number of iterations occurs.

9. The method of claim 1 wherein adaptively framing comprises re-binning based on the first measure, the first measure comprising an amount of motion and/or a body mass index of the patient.

10. The method of claim 9 further comprising estimating the amount of motion from the counts, wherein a number of iterations in the reconstructing is based on the count density and the amount of motion.

11. The method of claim 10 further comprising controlling smoothing of the representation based on the amount of motion.

12. The method of claim 1 wherein adaptively framing comprises re-binning based on a task or application for the acquiring from the patient.

13. The method of claim 12 further comprising receiving an indication of the application for the acquiring, and establishing a number of iterations in the reconstructing based on the application and a count density.

14. A method for controlling reconstruction in an emission tomography system, the method comprising:
   receiving an application for imaging the patient;
   determining a reconstruction-related characteristic of detected emissions, the reconstruction-related characteristic comprising motion or body mass index determined prior to reconstruction;

setting a value of a reconstruction parameter based on the reconstruction-related characteristics;
reconstructing a representation from the emissions using the value of the reconstruction parameter; and
generating an image from the representation; and
wherein determining further comprises determining a count density, a pixel size for framing counts of the detected emissions set based on the count density.

15. The method of claim 14 wherein receiving the application comprises receiving a type of emission tomography scan, and wherein setting the value comprises setting the value based on the type of emission tomography scan.

16. The method of claim 14 wherein setting comprises setting a number of iterations in the reconstructing.

\* \* \* \* \*